United States Patent [19]

Grasser

[11] Patent Number: 4,811,725

[45] Date of Patent: Mar. 14, 1989

[54] EXTRACORPOREAL LITHOTRIPSY APPARATUS

[75] Inventor: Franz Grasser, Eggolsheim, Fed. Rep. of Germany

[73] Assignee: Siemens Aktiengesellschaft, Berlin and Munich, Fed. Rep. of Germany

[21] Appl. No.: 115,046

[22] Filed: Oct. 30, 1987

[30] Foreign Application Priority Data

Dec. 22, 1986 [DE] Fed. Rep. of Germany ....... 3643976

[51] Int. Cl.$^4$ ............................................. A61B 17/22
[52] U.S. Cl. ................................... 128/24 A; 128/328
[58] Field of Search ............. 128/653, 328, 660, 24 A; 378/205, 901, 197, 195, 208

[56] References Cited

U.S. PATENT DOCUMENTS 4,237,901 12/1980 Taenzer .
4,669,483 6/1987 Hepp et al. .
4,674,505 6/1987 Pauli et al. .

FOREIGN PATENT DOCUMENTS 3220751 12/1983 Fed. Rep. of Germany ...... 128/328
3343924 6/1985 Fed. Rep. of Germany .
57-151938 9/1982 Japan .
1546926 5/1979 United Kingdom .

OTHER PUBLICATIONS

"Computerized Patient Contours Using the Scanning Arm of a Compound B—Scanner", Hills et al., Med. Phys. 6(4), Jul., Aug. 1979, pp. 309–311.

*Primary Examiner*—Ruth S. Smith

[57] ABSTRACT

An extracorporeal lithotripsy apparatus includes at least one shock wave tube for generating focussed shock waves at a location in the body of a patient at which a calculus is disposed for disintegrating the calculus. The shock wave tube has a deformable portion which conforms to the shape of the patient when the shock wave tube is pressed against the patient and a rigid portion which supports the deformable portion. The apparatus also includes a system for positioning the shock wave tube at a location against the patient such that the calculus is disposed at the focus. The shock wave tube is provided with a sensor and a detector circuit which generates a signal upon the occurrence of contact between the patient and the rigid portion of the shock wave tube so as to cease operation of the positioning system so that the patient is not displaced by movement of the shock wave tube.

11 Claims, 2 Drawing Sheets

EXTRACORPOREAL LITHOTRIPSY APPARATUS

BACKGROUND OF THE INVENTION

1. Field of the Invention

The present invention relates to extracorporeal lithotripsy devices, and in particular to such devices which utilize a locating system, such as an x-ray or ultrasound system, top identify the position of the calculus within the patient and to control a positioning system for the shock wave tube so as to position the shock wave tube such that its focus is coincident with the calculus.

2. Description of the Prior Art

Lithotripsy devices are known which include a shock wave tube for generating shock waves focussed at a location disposed a distance in front of the shock wave tube. The shock wave tube includes a rigid portion and a deformable portion filled with coupling fluid, and means for positioning the shock wave tube at the exterior of a patient so that the deformable portion is pressed against the patient to conform to the patient's body, with the focus of the shock wave tube and the calculus being coincident. The shock wave tube and the patient support table may be moved relative to each other for this purpose by the positioning system. A locating system is also provided for identifying the position of the calculus within the patient, such as an x-ray system or an ultrasound system. A visual display is provided by the locating system which includes a mark identifying the calculus and an indicator for the position of the focus. Devices of this type are utilized, for example, for disintegrating kidney stones in situ in the human body, and have the advantage of avoiding invasion of the body using instruments.

Such an apparatus is described, for example, in German OS No. 33 28 051, corresponding to U.S. Pat. No. 4,674,505. This apparatus includes a shock wave tube having a tubular jacket, a flat coil, and a copper membrane separated from the flat coil by an insulating foil. An acoustic convergent lens is disposed in the tubular jacket which focusses the planar shock waves generated by the membrane to a focal point. For coupling the shock wave tube to the patient, the opening of the tubular jacket at the opposite end from the membrane is closed with a deformable cover. The volume between the cover and the membrane is filled with a coupling fluid. As the shock wave generator is moved toward the patient until the calculus to be disintegrated is situated at the focus of the lens arrangement, the cover is pressed against the surface of the patient and is deformed thereby, so that the space behind the cover within the shock wave tube is completely filled with coupling fluid, so that the shock waves will always propogate within the fluid.

For obese patients, however, it is possible that the calculus to be destroyed is so far inside the body of the patient that the focal distance of the lens arrangement is not adequate. As a result, during the automatic positioning of the shock wave tube with respect to the patient, the rigid portion of the shock wave tube, or the lens arrangement, may come into contact with the patient. Since coincidence of the focal point and the calculus has not been achieved, the positioning system will continue to try to move the shock wave tube to bring about such coincidence, with the result of pushing the patient and thus displacing the calculus from its original position, which was used as the basis for positioning the shock wave tube. Since the calculus has now been moved from this original position, all subsequent positioning of the shock wave tube is no longer accurate.

SUMMARY OF THE INVENTION

It is an object of the present invention to provide an extracorporeal lithotripsy apparatus wherein the range of applications of the shock wave tube is expanded.

It is a further object of the present invention to provide such an apparatus which permits treatment of obese patients.

The above objects are achieved in accordance with the principles of the present invention in a lithotripsy apparatus wherein the shock wave tube is provided with a sensor which recognizes when the patient is touched by the rigid part of the shock wave tube, and which generates an interrupt signal to the positioning system for the shock wave tube. The patient has been previously positioned so that the calculus therein is at a known location in space. The movement of the shock wave tube against the patient is thus stopped before the shock wave tube is forced against the patient to such an extent that the patient, and the calculus therein, are moved. The position of the calculus is thus not displaced from the known location.

Contact between the patient and the rigid portion of the shock wave tube can be identified by various types of sensors. The sensor may, for example, be an ultrasound range finder or a switch acuatable with a ram. In a preferred embodiment, an elastic hollow member, which may be filled with gas, is disposed in the volume of the shock wave tube occupied by the coupling fluid and connected to a source of compressed air so that normally the contact pressure of the shock wave tube against the patient is at a constant value. A pressure sensor is provided which generates a signal when a selected contact pressure is exceeded, indicating that the shock wave tube is about to be pushed too strongly against the patient.

Shock waves can be triggered by means of a computer connected to the sensor through a detector circuit, the computer being connected to the locating apparatus and to a displacement transducer for the moveable components. Given a signal generated by the sensor and the detector circuit, the computer identifies on the basis of the displacement required for optimum coupling whether the calculus identified by the locating apparatus is within the effective disintegrating region of the shock wave tube. Circuitry can be provided for generating a marker indicating the position of the tube focus, the marker being mixed with the video signal for the image of the calculus so that the attending technician or physician can visually discern when the focus and the calculus are close enough together to be within the effective disintegrating region of the shock wave tube. The attending technician or physician can also check the coupling procedure through the computer if the computer is connected to the circuitry which generates the marker, and controls that circuitry for displacing the marker. The shock wave tube can be moved to a stable final position by the computer which is connected to the drive circuitry for the positioning system for the patient support so that the position of the patient is shifted in a manner which permits continuation of the coupling procedure. The patient support may alternatively be manually displaced by providing the computer with means for generating and displaying the coordinates of the patient support on the display.

DESCRIPTION OF THE PREFERRED EMBODIMENTS

Figure 1:
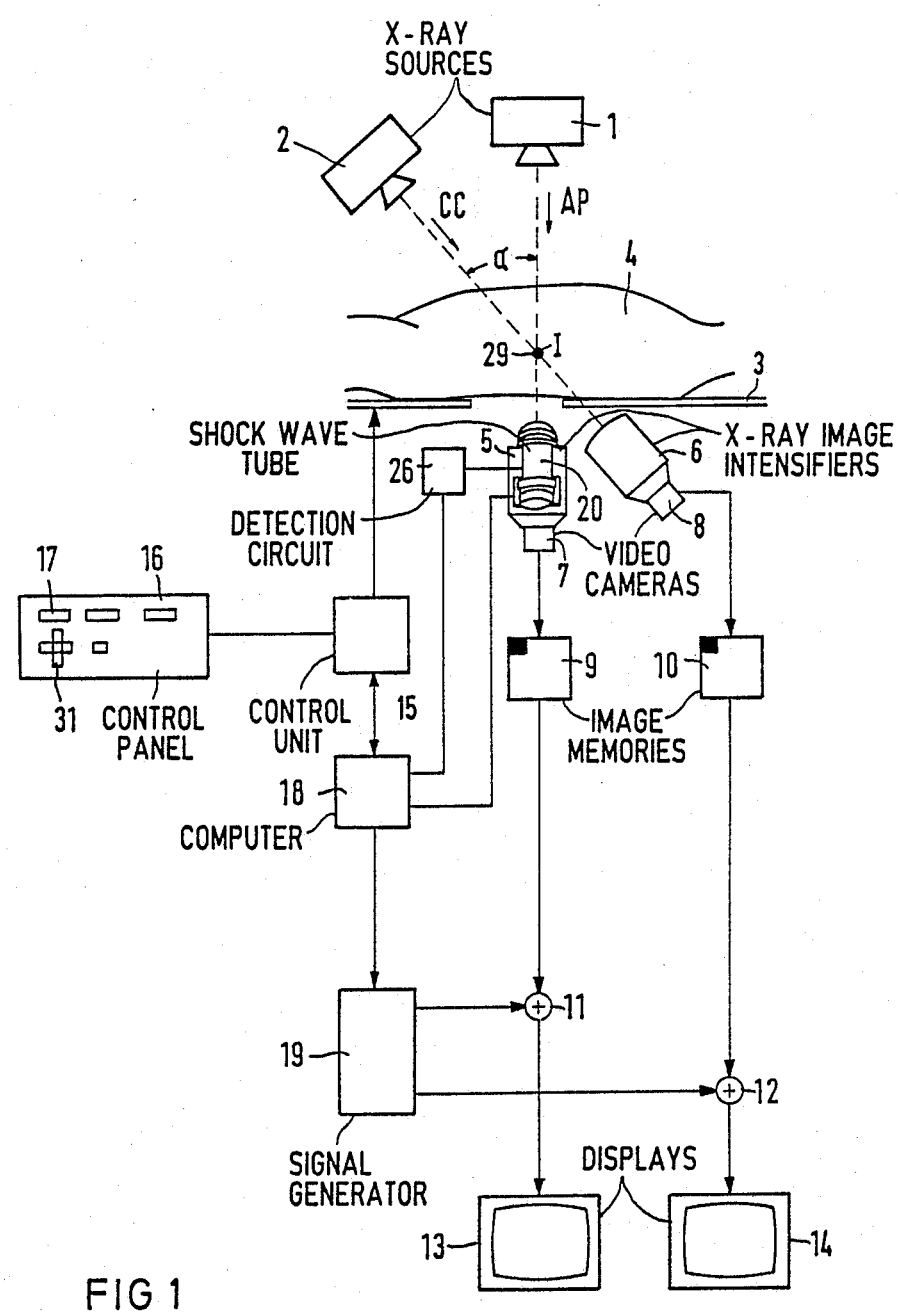
FIG. 1 is a schematic block diagram of an extracorporeal lithotripsy apparatus constructed in accordance with the principles of the present invention.

A lithotripsy work station is shown in FIG. 1 constructed in accordance with the principles of the present invention which includes an x-ray installation used as a locating means for identifying the position of a calculus 29 within the body of a patient 4. The x-ray installation includes two x-ray sources 1 and 2 which generate respective x-ray beams penetrating the patient 4, who is disposed on a patient support 3. The x-ray beams are incident on the input luminescent screens of respective x-ray image intensifiers 5 and 6. The x-ray source 1 and the x-ray image intensifier 5 may be disposed such that a central ray of the x-ray beam from the x-ray source 1 is perpendicularly incident on the patient 4 (a.p. projection). The x-ray source 2 and the x-ray image intensifier 6 may be obliquely disposed such that a central ray from the x-ray source 2 intersects the central ray from the x-ray tube 1 at the isocenter I within the patient 4 at an angle $\alpha$ of, for example, 45° (c.c. projection).

Transillumination images from the two different projection directions are thus obtained, so that the patient 4 can be 3-dimensionally shifted by means of moving the patient support 3 so that the calculus 29, for example, a kidney stone, is situated at the isocenter I.

The output signals of video cameras 7 and 8, respectively coupled to the x-ray image intensifiers 5 and 6, are entered into two image memories 9 and 10. The outputs of the image memories 9 and 10 are connected to respective first inputs of addition stages 11 and 12, each having an output supplied to respective monitors 13 and 14 on which the reproduced x-ray image is displayed.

After the conclusion of the transillumination phase with the x-ray sources 1 and 2, the x-ray images are converted into video signals via the image intensifiers 5 and 6 and the video cameras 7 and 8, which signals are entered into the memories 9 and 10. As explained in detail below, these video signals have a signal mixed therewith in the addition stages 11 and 12, so that the x-ray images with the mixed signal are displayed on the monitors 13 and 14.

The patient support 3 is connected to a control unit 15 for motor-driven 3-dimensional displacement of the patient support 3. The patient support 3 may be displaced via a control panel 16, which may include a display 17 for the three spatial coordinates. A computer 18 is connected to the control unit 15, as well as to a signal generator 19. The signal generator 19 generates a marker which is mixed with the signals from the memories 9 and 10 in the addition stages 11 and 12 so as to be combined with the x-ray image on the displays 13 and 14.

Figure 3:
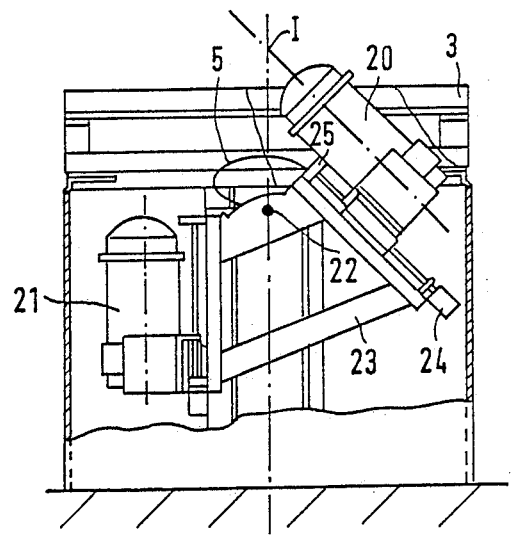
FIG. 3 is a detailed side view of the arrangement for positioning the shock wave tubes in the apparatus of FIG. 1.

Shock wave tubes 20 and 21 are arranged beneath the patient support 3, one of which can be seen in FIG. 1 and both of which can be seen in detail in FIG. 3. The shock wave tubes 20 and 21 may be pivoted from a standby position to a position wherein one of the tubes is coupled to the patient 4. The shock wave tubes 20 and 21 are attached to a common mount 23 which is pivotable around an axis 22 extending parallel to the longitudinal axis of the patient support 3. The shock wave tubes are attached thereto such that the longitudinal axis of the shock wave tube 20, after pivoting, is aligned with the isocenter I. The shock wave tube 20 can be moved toward the patient 4 by a position adjustment element 24. When the shock wave tube 20 is moved so as to reach a detent 25, the isocenter I will be situated at the focus of the shock wave tube 20.

Figure 2:
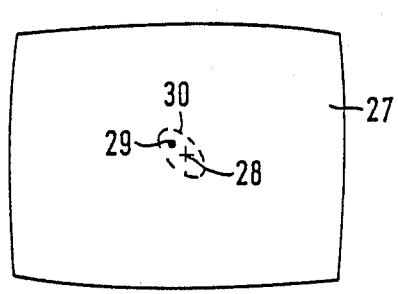
FIG. 2 is an example of a display image which can occur during the operation of the apparatus shown in FIG. 1.

If, however, the patient 4 is obese, the rigid portion of the shock wave tube 20 will come into contact with the patient 4 before the shock wave tube 20 touches the detent 25. If the shock wave tube 20 were then moved further toward the detent 25, the patient 4 would be pushed by this continued motion so that the calculus 29 would no longer be situated at the isocenter I, and a shock wave treatment could no longer be undertaken. To avoid such a situation, the shock wave tube 20 is provided with a sensor which is connected to a detector circuit 26, which supplies a signal to the computer 18 when contact between the patient 4 and the rigid portion of the shock wave tube 20 occurs. This signal stops the coupling procedure. The computer 18 may be connected to the position adjustment element 24, or to a different element (not shown) which provides a signal corresponding to the distance of the shock wave tube 20 from the patient 4. If the computer 18 is connected to the position adjustment element 24, this signal may be, for example, a signal corresponding to the amount of time that the adjustment element 24 has been operating to move the shock wave tube 20. From this signal, the computer 18 calculates the position of the focus of the shock wave tube 20 and drives the signal generator 19 so that a mark, such as a graticule 28, shown on the monitor screen 27 in FIG. 2, is displaced. The image of the calculus 29 is thus not coincident with the graticule 28, so that the attending physician can see that the coupling procedure was prematurely stopped. At the same time, the computer 18 calculates the effective disintegrating region of the shock wave tube 20, and again through the signal generator 19, causes an image 30 to be mixed with the video image signal showing this effective region. The attending physician can then see whether the calculus 29 is still disposed within the effective region 30, so that disintegration of the calculus 29 can still be undertaken by triggering the shock wave generator 20.

Alternatively, the computer 18 may calculate the required coordinates for the patient support 3, which are displayed to the attending physician either by the display 17 on the control panel 16, or via the monitor screen 27. The attending physician can then displace the patient support 3 by manually operating controls 31 on the control panel 16 so that the shock wave tube 20 can be moved to the detent 25 for complete coupling.

Displacement of the patient support 3, however, may also be undertaken automatically with the computer 18 directly operating the control unit 15.

Figure 4:
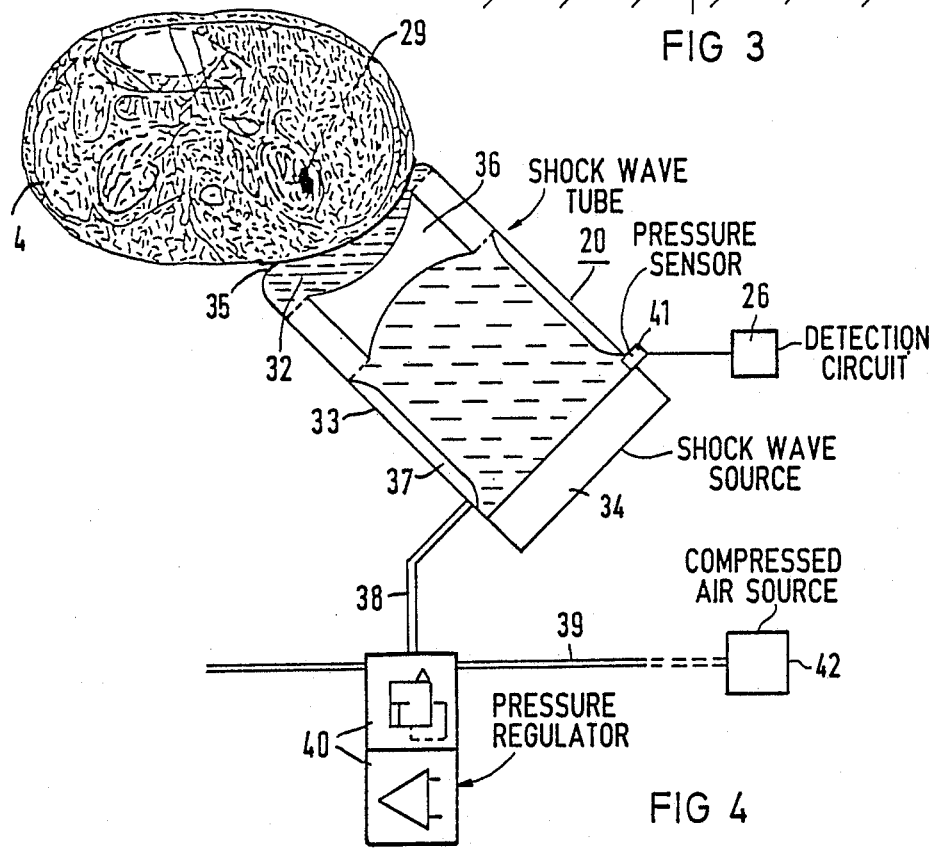
FIG. 4 is a schematic diagram showing a shock wave tube coupled to a patient in the apparatus of FIG. 1.

One embodiment for identifying contact between the patient 4 and the rigid portion of the shock wave tube 20 is shown in FIG. 4. In this embodiment, the shock wave tube 20 includes a tube jacket 33 filled with fluid 32. A shock wave source 34 is disposed at one end of the tube jacket 33. The opposite end of the tube jacket 33 is terminated by a flexible cover 35. The flexible cover 35 of the shock wave tube 20 is placed against the surface of the patient 4, as shown in cross-section in FIG. 4.

In this embodiment a calculus 29, for example, a kidney stone, is to be disintegrated. To this end, the planar shock waves generated by the shock wave generator 34 are focussed on the kidney stone 25 by an acoustic lens arrangement 36. The acoustic lens arrangement 36 is provided with suitable apertures or channels, indicated by dashed lines, providing fluid communication between the volumes in front of and behind the acoustic lens arrangement 36.

For setting and controlling the pressure of the fluid 32, and thus the contact pressure against the patient 4, an elastic hollow member 37 filled with gas, such as air, is provided in a portion of the volume provided by the fluid 32. The hollow member 37 may be in the form of an annular element pressing against the interior wall of the tube jacket 33. The interior of the hollow member 37 is connected to a pressure regulator 40 via a line 38, which in turn is connected to a compressed air source 42 via a line 39.

The pressure in the interior of the hollow member 37, and thus the pressure of the fluid 32 and the contact pressure against the patient 4, can be controlled, particularly by being maintained constant, with the use of the pressure regulator 40.

The volume and pressure of the gas supplied to the interior of the member 37 are selected such that if the patient 4 is so obese that the surface of the patient's body will come into contact with the rigid portion of the shock wave tube 20, for example, the lens arrangement 36, a substantial amount of the gas will be forced from the interior of the hollow member 37. If the shock wave tube 20 is then moved closer toward the body of the patient 4, the pressure within the shock wave tube 20 will be further increased, which will be recognized by a pressure sensor 41 connected to the detector circuit 26. This causes the detector circuit 26 to generate the aforementioned signal to the computer 18, which stops the coupling procedure and causes the further measures described above to be undertaken.

Instead of the pressure sensor 41 and the detector circuit 26, it is possible to use an ultrasound system as the detector, which is connected to the shock wave tube 20 and continually monitors the approach of the shock wave tube 20 to the patient by distance measurement.

It is also possible for detection to be undertaken by means of a switch actuated by a ram, with the ram being disposed to actuate the switch just before the patient 4 comes into contact with the rigid portion of the shock wave tube 20.

Although modifications and changes may be suggested by those skilled in the art it is the intention of the inventor to embody within the patent warranted hereon all changes and modifications as reasonably and properly come within the scope of his contribution to the art.

I claim as my invention:

1. An extracorporeal lithotripsy apparatus for disintegrating a calculus in the body of a patient comprising:
   means for positioning said patient so that said calculus is disposed at a known location in space;
   means for generating shock waves focussed at a focus, said means for generating shock waves having a region surrounding said focus effective for disintegrating said calculus, and said means for generating shock waves having a deformable portion adapted to be pressed against and conformable to a portion of the body of said patient, and a rigid portion;
   means for monitoring the position of said means for generating shock waves;
   means connected to said means for positioning and to said means for monitoring for moving said means for generating shock waves to press said deformable portion against said body to bring said said focus into substantial coincidence with said known location;
   means for sensing between said body and said rigid portion of said means for generating shock waves and for interrupting operation of said means for moving to cease movement of said means for generating shock waves upon the occurrence of said contact; and
   computer means with data identifying said effective region entered therein connected to said means for positioning and to said means for moving for calculating whether the calculus is within said effective region when said movement of said means for generating shock waves ceases.

2. An apparatus as claimed in claim 1, wherein said means for generating shock waves includes a housing, which includes said deformable portion and said rigid portion, filled with a fluid and wherein said means for sensing is a means in contact with said fluid for detecting changes in the pressure of said fluid.

3. An apparatus as claimed in claim 1, wherein said means for generating shock waves is a shock wave tube, which includes said deformable portion and said rigid portion, having a fluid-filled interior, said fluid having a contact pressure when said deformable portion is pressed against said portion of the body of said patient, and further comprising means in said shock wave tube for maintaining the contact pressure of said fluid at a constant value, and wherein said means for sensing is a means in contact with said fluid for generating a signal when a selected contact pressure is exceeded.

4. An apparatus as claimed in claim 3, wherein said means for maintaining said contact pressure constant is a hollow member disposed in said interior of said shock wave tube and connected to a compressed air source.

5. An apparatus as claimed in claim 1 further comprising means for visually displaying respective images corresponding to said calculus, said focus and said effective region.

6. An apparatus as claimed in claim 1 further comprising:
   means for generating a visual image of at least a portion of said body in which said calculus is disposed;
   means for generating a mark corresponding to the position of said means for generating shock waves; and
   means connected to said computer means for changing the position of said mark as said means for generating shock waves is moved.

7. An apparatus as claimed in claim 1, wherein said means for positioning includes:
   a patient support on which said patient is disposed; and
   means for displacing said patient support connected to said computer means for re-positioning said patient support and said patient thereon after movement of said means for generating shock waves has ceased.

8. An apparatus as claimed in claim 6, wherein said means for generating a visual image includes an x-ray system.

9. An apparatus as claimed in claim 8, wherein said x-ray system includes means for generating two images in respective planes of said patient, said planes intersecting at a line containing said calculus.

10. An apparatus as claimed in claim 1, wherein said means for positioning includes a patient support on which said patient is disposed and means for displacing said patient support and wherein said apparatus further comprises means connected to said computer means for displaying the coordinates of said patient support needed for optimum coupling of said patient with said means for generating shock waves.

11. An extracorporeal lithotripsy apparatus for disintegrating a calculus in the body of a patient comprising:
   means for positioning said patient so that said calculus is disposed at a known location in space;
   a shock wave tube for generating shock waves at a focus, said shock wave tube having a region surrounding said focus effective for disintegrating said calculus, said shock wave tube being filled with fluid at a pressure and having a deformable portion conformable to a portion of the body of said patient to acoustically couple said shock wave tube to said patient, and a rigid portion;
   means for monitoring the position of said shock wave tube;
   means connected to said means for positioning and to said means for monitoring for moving said shock wave tube to press said deformable portion against the body of said patient to couple said shock wave tube to said patient and to bring focus into substantial coincidence with said known location;
   means for maintaining the pressure of said fluid in said shock wave tube at a constant pressure during coupling of said shock wave tube to said patient;
   sensor means for generating a signal if the pressure of said fluid in said shock wave tube exceeds a selected value;
   means for interrupting operation of said means for moving said shock wave tube upon generating of said signal by said sensor means; and
   computer means with data identifying said effective region entered therein connected to said means for positioning and said means for moving for calculating whether the calculus is within said effective region when operation of said means for moving said shock wave tube is interrupted.

* * * * *